(12) United States Patent
Goodman et al.

(10) Patent No.: US 10,545,092 B2
(45) Date of Patent: Jan. 28, 2020

(54) AUTOMATED OPTICAL DEVICE MONITORING (71) Applicant: Alarm.com Incorporated, Tysons, VA (US)

(72) Inventors: Daniel Marc Goodman, Needham, MA (US); Craig Carl Heffernan, Oregon City, OR (US); Harrison Wayne Donahue, Attleboro, MA (US)

(73) Assignee: Alarm.com Incorporated, Tysons, VA (US)

( * ) Notice: Subject to any disclaimer, the term of this patent is extended or adjusted under 35 U.S.C. 154(b) by 256 days.

(21) Appl. No.: 15/804,521

(22) Filed: Nov. 6, 2017

(65) Prior Publication Data

US 2018/0128749 A1 May 10, 2018

Related U.S. Application Data (60) Provisional application No. 62/497,042, filed on Nov. 7, 2016.

(51) Int. Cl.
G01N 21/66 (2006.01)
G01N 21/88 (2006.01)
F21V 23/04 (2006.01)

(52) U.S. Cl.
CPC ......... *G01N 21/66* (2013.01); *F21V 23/0407* (2013.01); *G01N 21/8806* (2013.01)

(58) Field of Classification Search
CPC ........ G01N 21/00; G01N 21/62; G01N 21/66; G01N 21/84; G01N 21/88; G01N 21/8806; G01N 21/956; F24F 11/00; F24F 11/30; F24F 11/32; F24F 11/38; F24F 11/50; F24F 11/52; F21V 23/00; F21V 23/04; F21V 23/0407; G01R 31/00; G01R 31/28; G01R 31/302; G01R 31/308; G01R 31/317; G01R 31/31728; G01R 1/06; G01R 19/145; G01R 19/165
USPC ................... 324/500, 537, 750.23, 555, 556
See application file for complete search history.

(56) References Cited

U.S. PATENT DOCUMENTS

| 4,604,518 | A | 8/1986 | Payne |
| 6,411,198 | B1 | 6/2002 | Hirai et al. |
| 6,976,163 | B1 | 12/2005 | Hind et al. |
| 6,993,188 | B2 * | 1/2006 | Aoki ........................ G06K 9/46 382/190 |
| 7,091,471 | B2 | 8/2006 | Wenstrand et al. |
| 7,161,489 | B2 | 1/2007 | Sullivan et al. |
| 9,166,810 | B2 | 10/2015 | Oshima et al. |
| 10,129,395 | B1 * | 11/2018 | Maxwell ........... H04M 3/42042 |

(Continued)

Primary Examiner — Hoai-An D. Nguyen
(74) Attorney, Agent, or Firm — Fish & Richardson P.C.

(57) ABSTRACT

Techniques are described for using an optical sensor to monitor light produced by an indicator light of a monitoring system. The optical sensors can monitor attributes of the indicator light in order to detect a blink pattern outputted by the indicator light. In some implementations, video data indicating a blink pattern of a device within a property is obtained. One or more attributes of the blink pattern are identified based on processing the obtained video data. A status for the device is determined based at least on the one or more identified attributes. A system action that corresponds to the status is determined. The system action corresponding to the determined status is performed.

20 Claims, 4 Drawing Sheets (56) References Cited

U.S. PATENT DOCUMENTS

| | | | | |
|---|---|---|---|---|
| 2005/0117876 A1* | 6/2005 | Hosoi | ............... | G11B 27/034 386/224 |
| 2007/0286496 A1* | 12/2007 | Matsuzaki | ......... | H04N 1/00204 382/209 |
| 2014/0160250 A1* | 6/2014 | Pomerantz | ......... | H04N 5/23229 348/47 |

* cited by examiner

| LED COLOR | BLINK PATTERN | DEVICE MANUFACTURER | SYSTEM STATUS | SPECIFIED SYSTEM ACTION |
|---|---|---|---|---|
| RED | ━ ━ ━ | MANUFACTURER A | ROUTINE MAINTENANCE | UPDATE SERVICE RECORD FOR USER ACCOUNT |
| RED | ▬ ▬ ▬ ▬ ▬ | MANUFACTURER A | HIGH ALERT - COOLING SYSTEM | TRANSMIT NOTIFICATION TO USER |
| GREEN | ━━━━━━ | MANUFACTURER A | NO MAINTENANCE REQUIRED | UPDATE TRANSMISSION RECTORD (NO ALERT) |
| RED | ━ ━ • | MANUFACTURER B | ROUTINE MAINTENANCE | UPDATE SERVICE RECORD FOR USER ACCOUNT |
| RED | ━━━ ━ | MANUFACTURER B | HIGH ALERT - COOLING SYSTEM | TRANSMIT NOTIFICATION TO USER |
| GREEN | • • • • | MANUFACTURER B | NO MAINTENANCE REQUIRED | UPDATE TRANSMISSION RECORD (NO ALERT) |
| . . . | . . . | . . . | . . . | . . . |

302 — RED row 1
304 — RED row 2
306 — GREEN row 3
308 — RED row 4
310 — RED row 5
312 — GREEN row 6

```
┌─────────────────────────────────────────────────────────────────┐
│  OBTAIN DATA COLLECTED BY AN OPTICAL DEVICE WITHIN A PROPERTY   │
│                                                             410 │
└─────────────────────────────────────────────────────────────────┘
                                 │
                                 ▼
┌─────────────────────────────────────────────────────────────────┐
│ IDENTIFY ONE OR MORE ATTRIBUTES ASSOCIATED WITH A BLINK PATTERN │
│      OF A OUTPUT DEVICE WITHIN THE OBTAINED DATA                │
│                                                             420 │
└─────────────────────────────────────────────────────────────────┘
                                 │
                                 ▼
┌─────────────────────────────────────────────────────────────────┐
│ DETERMINE A STATUS ASSOCIATED WITH THE OUTPUT DEVICE BASED ON   │
│              THE IDENTIFIED ATTRIBUTES                          │
│                                                             430 │
└─────────────────────────────────────────────────────────────────┘
                                 │
                                 ▼
┌─────────────────────────────────────────────────────────────────┐
│  PERFORM A SYSTEM ACTION BASED ON THE DETERMINED STATUS         │
│              ASSOCIATED WITH THE OUTPUT DEVICE                  │
│                                                             440 │
└─────────────────────────────────────────────────────────────────┘
```

FIG. 4

AUTOMATED OPTICAL DEVICE MONITORING

CROSS-REFERENCE TO RELATED APPLICATION

This application claims the benefit of U.S. Provisional Patent Application No. 62/497,042, filed on Nov. 7, 2016, and titled "AUTOMATED OPTICAL DEVICE MONITORING," which is incorporated herein by reference in its entirety.

TECHNICAL FIELD

This disclosure application relates generally to monitoring systems.

BACKGROUND

Monitoring systems such as heating, ventilating and air conditioning (HVAC) systems for a property often include one or more light-emitting diode (LED) indicators that provide a system status. For example, LED indicators can use blink patterns to indicate various problems related to the operation of the system. A service technician can use a blink pattern to manually diagnose a system fault based on observing a sequence of the blink pattern, or based on lights turning on and off.

SUMMARY

Techniques are described for using an optical sensor to monitor light produced by an indicator light of a monitoring system. The optical sensors can monitor attributes of the indicator light in order to detect a blink pattern outputted by the indicator light. Detected blink patterns can then be reproduced electronically and used to automatically identify a corresponding system status associated with the detected blink patterns. The system status can be identified using a blink pattern repository that classifies previously detected blink patterns based on system information and indicates a severity of a problem condition associated with each blink pattern. The system can then perform a specified system action in response to identifying system status information for a detected blink pattern that matches a blink pattern stored within the repository. For example, in response to detecting a system status descriptive of a failure condition, the system can automatically transmit alert notifications to service providers prior to a complete system malfunction taking place.

Implementations of the described techniques may include hardware, a method or process implemented at least partially in hardware, or a computer-readable storage medium encoded with executable instructions that, when executed by a processor, perform operations.

The details of one or more implementations are set forth in the accompanying drawings and the description below. Other features will be apparent from the description and drawings, and from the claims.

DESCRIPTION OF DRAWINGS

In the drawings, like reference numbers represent corresponding parts throughout.

DETAILED DESCRIPTION

In general, techniques are described for using an optical sensor to monitor light produced by an indicator light of a monitoring system. The optical sensors can monitor attributes of the indicator light in order to detect a blink pattern outputted by the indicator light. Detected blink patterns can then be reproduced electronically and used to automatically identify a corresponding system status associated with the detected blink patterns. The system status can be identified using a blink pattern repository that classifies previously detected blink patterns based on system information and indicates a severity of a problem condition associated with each blink pattern. The system can then perform a specified system action in response to identifying system status information for a detected blink pattern that matches a blink pattern stored within the repository. For example, in response to detecting a system status descriptive of a failure condition, the system can automatically transmit alert notifications to service providers prior to a complete system malfunction taking place.

Figure 1:
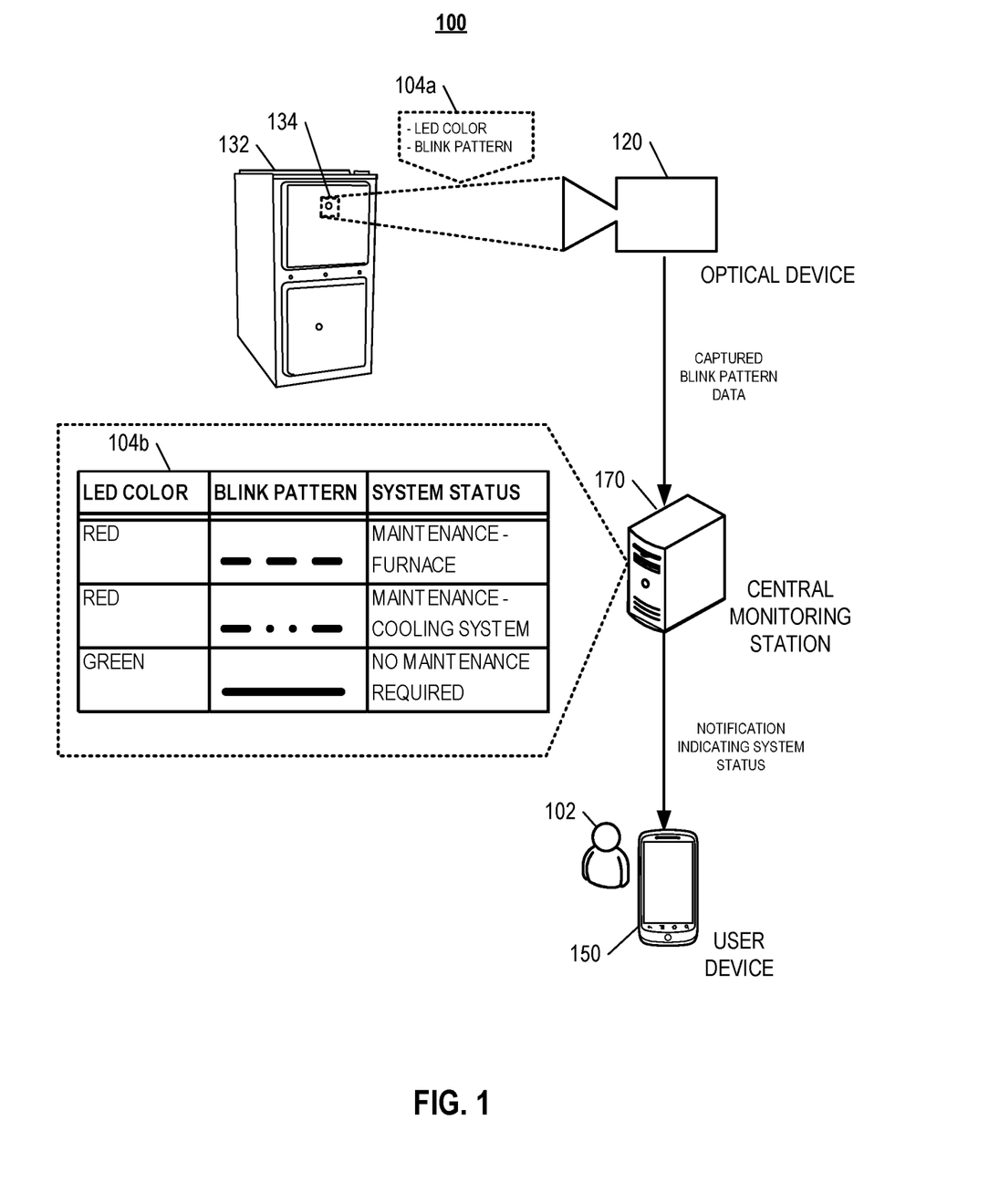
FIG. 1 illustrates an example of a process for analyzing blink pattern data of a monitoring system.

FIG. 1 illustrates an example of a process for analyzing blink pattern data of a monitoring system. An optical device 120 initially captures blink pattern data 104a produced by an LED indicator 134 of an output device 132 associated with an HVAC system. The output device 132 can be, for example, a HVAC unit that provides a status output, a control panel of an HVAC system, or any other type of status output device of any type of monitoring device (e.g., alarm security system). The captured light data 104a can include, for example, a wavelength of light or a blink pattern associated with the light produced by the LED indicator 134. The captured blink pattern data 104a is then transmitted to a central monitoring station 170 that stores a blink pattern repository 104b. The central monitoring station 170 then mappings included within blink pattern repository 104b to identify a system status corresponding to the blink pattern included within the blink pattern data 104a. The central monitoring station 170 can then perform a designated system action based on the system status, e.g., transmitting a notification indicating the system status. The output device 132 may be placed in various locations of a property. In some instances, the output device 132 represents a monitoring panel associated with the HVAC system that is placed inside a property. Additionally, or alternatively, the output device 132 represents device placed outside of the property (e.g., an HVAC condenser unit).

In the example depicted in FIG. 1, the color of light produced and the blink pattern indicated within the blink pattern data 104a can be used to identify a possible fault condition associated with a HVAC system. For example, a detected red color light with a consistent intermittent blink pattern can be used to indicate that maintenance for a furnace of the HVAC system may be necessary, whereas a detected red color light with an alternating blink pattern can be used to indicate that maintenance for a cooling system of the HVAC system may be necessary. In response to identifying the applicable system status, the central monitoring station 170 then transmits an alert notification to a user device 150 associated with a user 102 of the property in which the monitoring system is located. In other instances, the alert notification can be transmitted to another entity associated with the property such as, for example, a service provider or a manufacturer of the monitoring system.

Figure 3:
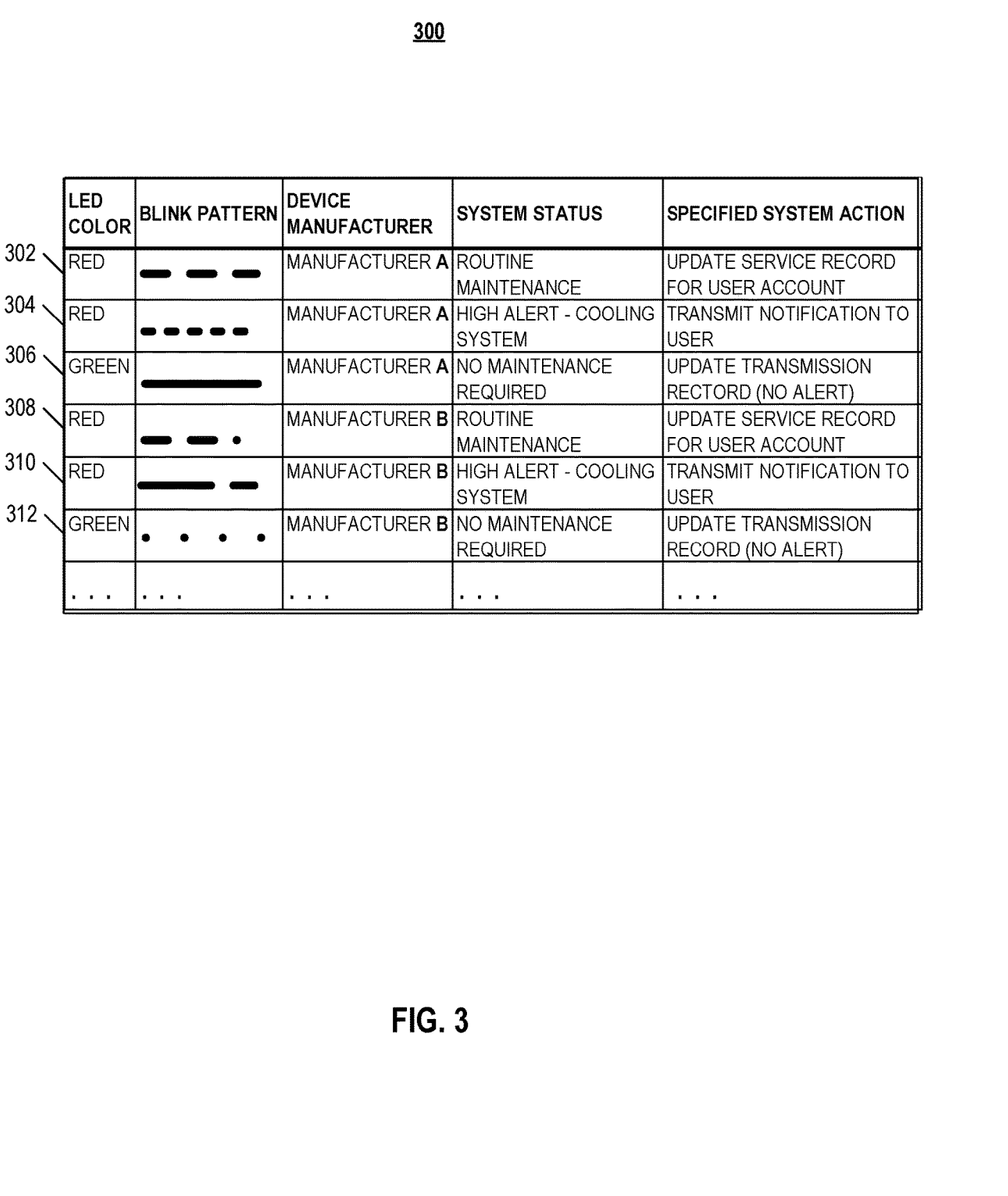
FIG. 3 illustrates an example of a blink pattern repository.

The collected blink pattern data 104a can be used to proactively identify deteriorating system performance prior to a total system failure that requires an entire system or component replacement. For example, by identifying blink patterns indicating insufficient detected performance for individual components, the central monitoring station 170 can identify problematic conditions that can be addressed by performing maintenance operations prior to seasonal changes when significant stress is placed on a monitoring system. Examples of visible indicators and corresponding system status conditions are illustrated in FIG. 3.

Figure 2:
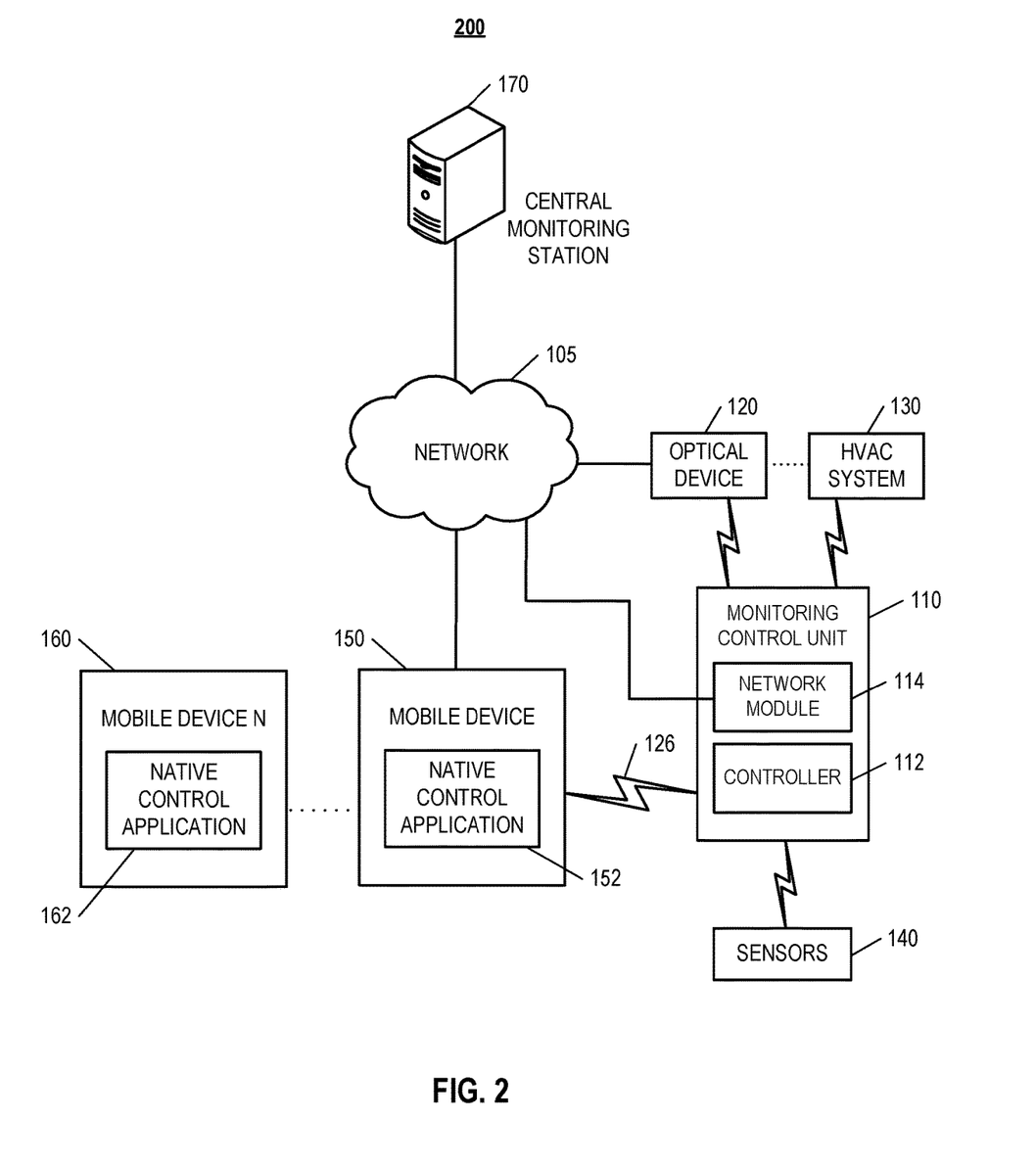
FIG. 2 illustrates an example of a system that is capable of collecting and analyzing blink pattern data.

FIG. 2 illustrates an example of a system 100 that is capable of collecting and analyzing blink pattern data. The system 100 may include a monitor control unit 110, an optical device 120, an HVAC system 130, one or more user devices 150, 160, and a central monitoring station 170 connected over a network 105. The components of the system 100 may exchange communications over the network 105.

In general, the system 100 enables proactive identification of possible failure conditions of a monitoring system prior to a total system failure due to cumulative performance deterioration. For instance, the optical device 120 can be configured to monitor the light produced by an LED indicator of the HVAC system 130 (or any other monitoring device associated with the system 100). The collected data can then be used to identify a blink pattern produced by the LED indicator. A blink pattern repository (illustrated in FIG. 3) stored on the central monitoring station 170 is then used to identify a corresponding system status for the blink pattern in order to perform a system action to reduce risks associated with the identified system status. Although the operations of the system are described with respect to HVAC system components, in some instances, similar techniques may be used to monitor and/or diagnose issues related to the functioning of other types of monitoring systems that are used within a property.

Referring now to the components of the system 100, the network 105 may be configured to enable exchange of electronic communications between devices illustrated in FIG. 2. For example, the network 105 may be configured to enable exchange of electronic communications between the monitor control unit 110, the optical device 120, the HVAC system 130, the sensors 140, the mobile devices 150, 160, or the central monitoring station 170.

The network 105 may include, for example, one or more of the Internet, Wide Area Networks (WANs), Local Area Networks (LANs), analog or digital wired and wireless telephone networks (e.g., a public switched telephone network (PSTN), Integrated Services Digital Network (ISDN), a cellular network, and Digital Subscriber Line (DSL)), radio, television, cable, satellite, or any other delivery or tunneling mechanism for carrying data. The network 105 may include multiple networks or subnetworks, each of which may include, for example, a wired or wireless data pathway.

The network 105 may also include a circuit-switched network, a packet-switched data network, or any other network able to carry electronic communications (e.g., data or voice communications). For example, the network 105 may include networks based on the Internet protocol (IP), asynchronous transfer mode (ATM), the PSTN, packet-switched networks based on IP, X.25, or Frame Relay, or other comparable technologies and may support voice using, for example, VoIP, or other comparable protocols used for voice communications. The network 105 may include one or more networks that include wireless data channels and wireless voice channels. The network 105 may be a wireless network, a broadband network, or a combination of networks including a wireless network and a broadband network.

The monitor control unit 110 may be an electronic device that coordinates and/or monitors the operations of the components of the system 100 through a set of data transmissions with each of the components of the system 100. The monitor control unit 110 includes a controller 112 and a network module 114. The controller 112 is configured to control the system 100 (e.g., a home alarm or security system) that includes the monitor control unit 110. In some examples, the controller 112 may include a processor or other control circuitry configured to execute instructions of a program that controls operation of an alarm system. In these examples, the controller 112 may be configured to receive input from sensors, detectors, or other devices included in the alarm system and control operations of devices included in the alarm system or other household devices (e.g., a thermostat, an appliance, lights, etc.). For example, the controller 112 may be configured to control operation of the network module 114 included in the monitor control unit 110.

The network module 114 is a communication device configured to exchange communications over the network 105. The network module 114 may be a wireless communication module configured to exchange wireless communications over the network 105. For example, the network module 114 may be a wireless communication device configured to exchange communications over a wireless data channel and a wireless voice channel. In this example, the network module 114 may transmit alarm data over a wireless data channel and establish a two-way voice communication session over a wireless voice channel. The wireless communication device may include one or more of a LTE module, a GSM module, a radio modem, cellular transmission module, or any type of module configured to exchange communications in one of the following formats: LTE, GSM or GPRS, CDMA, EDGE or EGPRS, EV-DO or EVDO, UMTS, or IP.

The network module 114 may also be a wired communication module configured to exchange communications over the network 105 using a wired connection. For instance, the network module 114 may be a modem, a network interface card, or another type of network interface device. The network module 114 may be an Ethernet network card configured to enable the monitor control unit 110 to communicate over a local area network and/or the Internet. The network module 114 also may be a voice-band modem configured to enable the alarm panel to communicate over the telephone lines of Plain Old Telephone Systems (POTS).

The monitor control unit 110 also may include a communication module that enables the monitor control unit 110 to communicate other devices of the system 100. The communication module may be a wireless communication module that allows the monitor control unit 110 to communicate wirelessly. For instance, the communication module may be a Wi-Fi module that enables the monitor control unit 110 to communicate over a local wireless network at the property. The communication module further may be a 900 MHz wireless communication module that enables the monitor control unit 110 to communicate directly with a monitor control unit. Other types of short-range wireless communication protocols, such as Bluetooth, Bluetooth LE, Zwave, ZigBee, etc., may be used to allow the monitor control unit 110 to communicate with other devices in the property.

In some examples, the monitor control unit 110 may include data capture and recording devices. In these examples, the monitor control unit 110 may include one or more motion sensors, one or more microphones, one or more biometric data collection tools, one or more temperature sensors, one or more humidity sensors, one or more air flow sensors, and/or any other types of sensors that may be useful in capturing monitoring data related to the property and users in the property.

The monitor control unit 110 further may include processor and storage capabilities. The monitor control unit 110 may include any suitable processing devices that enable the monitor control unit 110 to operate applications and perform the actions described throughout this disclosure. In addition, the monitor control unit 110 may include solid state electronic storage that enables the monitor control unit 110 to store applications, configuration data, collected sensor data, and/or any other type of information available to the monitor control unit 110.

The monitor control unit 110 may exchange communications with the optical device 120, the HVAC system 130, the sensors 140, the one or more mobile devices 150, 160, and the central monitoring station 170 using multiple communication links. The multiple communication links may be a wired or wireless data pathways configured to transmit signals from the optical device 120, the HVAC system 130, the sensors 140, the one or more mobile devices 150, 160, and the central monitoring station 170 to the controller 112. The optical device 120, the HVAC system 130, the sensors 140, the one or more mobile devices 150, 160, and the central monitoring station 170 may continuously transmit sensed values to the controller 112, periodically transmit sensed values to the monitor control unit 110, or transmit sensed values to the monitor control unit 110 in response to a change in a sensed value.

In some implementations, the monitor control unit 110 may locally monitor the operation of the electronic devices of the system 100 such the optical device 120, the HVAC system 130, the sensors 140, the one or more mobile devices 150, 160, and the central monitoring station 170. For instance, the monitor control unit 110 may enable or disable the devices of the system 100 based on a set of rules associated with energy consumption, user-specified settings, and/or other information associated with the conditions near or within the property where the system 100 is located. In some examples, the monitor control unit 110 may be used as a replacement to a traditional security panel that is used to monitor and control the operations of the system 100. In other examples, the monitor control unit 110 may coordinate monitoring operations with a separate security panel of the system 100. In such examples, the monitor control unit 110 may monitor particular activities of the devices of the system 100 that are not monitored by the security panel, or monitor the operation of particular devices that are not monitoring by the security panel.

The optical device 120 may be any type of recording device that is capable of capturing video footage of an output device associated with the HVAC system 130. For instance, as described previously with respect to FIG. 1, the optical device 120 captures video footage of the LED indicator 134 that produces a blink pattern by turning the LED on and off at certain frequencies and intervals. The optical device 120 can be used to capture raw video footage with the LED indicator 134 within its field of view such that the raw video footage can be processed in order to extract blink pattern data 104a.

The optical device 120 may include various hardware components. For instance, the optical device 120 may include a processor, a display, sensors, and input devices. In some implementations, the optical device 120 is capable to executing native applications that enable users to interact with a user interface in specific ways to control the operation of the optical device 120, or perform other monitoring operations related to the components of the system 100. For example, the native application may enable users to configure the frequency of monitoring of the output device of the HVAC system 130. As an example, the optical device 120 can be configured to periodically monitor an LED indicator of the output device, but only capture video footage once a blink pattern and/or light produced by the LED indicator is detected within the field of view of the optical device 120. In this example, selective capture by the optical device 120 can be used to minimize storage requirements for blink pattern data and/or conserve energy consumption associated with capturing blink pattern data.

In some implementations, the optical device 120 may communicate with the monitor control unit 110 via a wireless or wired communication link. For instance, the optical device 120 can communicate with the monitoring control unit 110 using various local wireless protocols, such as Wi-Fi, Bluetooth, Z-Wave, ZigBee, HomePlug (Ethernet over powerline), or wired protocols such as Ethernet, USB, and other wired protocols based on the RS232, RS485, and/or RS422 standards. The optical device 120 can also connect locally to other components of the system 100 (e.g., the HVAC system 130, the sensors 140, the one or more mobile devices 150, 160). The local connection can improve the speed of communications because communicating through the network 105 with a remote server (e.g., the central monitoring station 170), can be slower.

In some implementations, the optical device 120 is an aftermarket device that is either provided separately from the HVAC system 130, or purchased independently of the HVAC system 130. In such implementations, the optical device 120 can be, for example, a camera that is mounted directed onto the output device of the HVAC system 130 such that an LED indicator associated with the HVAC system 130 is within the field of view of the optical device 120. As an example, the optical device 120 can be a mountable wireless-enabled security camera that is capable of capturing video footage for extended periods of time and periodically uploading captured video footage to a local or remote storage device.

Additionally, or alternatively, instead of being a separate component within the system 100, the optical device 120 may instead be one of the mobile devices 150, 160. In such implementations, the mobile devices 150, 160 may run a native application that is capable of capturing video footage of the property and rendering visualizations that represent device information onto the screen of the mobile devices 150, 160. For example, the native application may utilize optical recognition techniques to detect a presence of one of the connected devices within the field of view of the captured video footage, and then use the processing capabilities of the mobile devices 150, 160 to render the visualizations onto the screen of the mobile devices 150, 160. In such an example, the user 102 may adjust the field of view by moving the mobile devices 150, 160 relative to the locations of the sensors 140.

The HVAC system 130 generally includes one or more components that monitor the heating, cooling and ventilation operations related to a property in which the system 100 is located. For example, components of the HVAC system 130 may operate to provide air quality control (e.g., ventilation, cleaning), provide temperature control (e.g., heating, cooling), provide humidity control (e.g., dehumidification, humidification), and/or temperature control (e.g., cooling, heating). In addition, the HVAC system 130 may include external or internal monitoring devices that periodically monitor the operations of individual components to ensure that they are functioning properly. In some instances, the monitoring devices can include one or more of the sensors 140 and/or the monitor control unit 110.

The HVAC system 130 additionally includes an output device that includes an LED indicator (e.g., the LED indicator 134) for providing a system status. In some instances, the output device can be included on a control panel placed on the exterior of a HVAC unit that are connected to air ducts. In such instances, the control panel can be directly accessed by service personnel when performing a maintenance operation. In other instances, the output device can be positioned on other components and/or devices that are associated with the HVAC system 130. For example, the output device can be placed on a thermostat that allows the user to control the heating and cooling operations of the HVAC system 130. In other examples, the output device can be placed in a designated regions of the property separate from where the HVAC system 130 is located.

The sensors 140 can include various types of monitoring devices that are placed within a property in which the system 100 is located. The sensors 140 may include components of a monitoring system (e.g., a security system for the property), or other separate smart devices that are configured to exchange communications over the network 105. For example, the sensors 140 may include one or more cameras, appliances, HVAC components, or other components that are installed and/or configured to operate within the property.

In general, the sensors 140 may be configured to monitor and/or control various aspects of the property. For example, cameras and/or sensors associated with the system 100 may be configured to monitor activity and/or conditions in various regions of the property (e.g., at various indoor or outdoor locations of the property). Cameras included within the sensors 140 can include various video, still-image, infrared, night-vision, or other cameras that are configured to monitor activity at a property. Sensors within the sensors 140 may include various activity sensors, such as motion sensors, contact sensors, etc., or may additionally or alternatively include various environmental sensors, such as temperature sensors, humidity sensors, noise sensors, light sensors, air quality sensors, smoke detectors, carbon monoxide detectors, water sensors, rain sensors, wind sensors, etc. Other components associated with the sensors 140 may include door and window locks, furnaces, air conditioners, ovens and stovetops, fans, garage doors, etc.

The sensors 140 may communicate with the monitor control unit 110 over communications links. The communication links can be a wired or wireless data pathway configured to transmit signals from the sensors 140 to the monitor control unit 110. The sensors 140 can continuously transmit and receive data from the controller 112, can periodically transmit and receive data from the controller 112, or can transmit and receive data from the controller 112 in response to detecting events, e.g., in response to detecting a change in a sensed value by a sensor of the monitoring system. The cameras, sensors, and other components of the monitoring system that are in communication with the monitor control unit 110 via the sensors 140 can continuously or periodically transmit and receive information from the sensors 140, or can transmit and receive information from the sensors 140 in response to detecting a specific event (e.g., an event at the property or an error relating to one or more of the cameras, sensors, or other components).

In some implementations, the sensors 140 can communicate directly with the central monitoring station 170 over the Internet without communicating through the monitor control unit 110. For example, the central monitoring station 170 may communicate with a camera, sensor, or other component to send and/or receive information related to controlling the camera, sensor, or component, information identifying the status of the camera, sensor, or component, or other information. In some instances, the central monitoring station 170 may communicate information directly to one or more cameras, sensors, and/or other components.

The one or more mobile devices 150, 160 may be devices that execute one or more native applications (e.g., native control applications 142, 152). The one or more mobile devices 150, 160 may be cellular phones or non-cellular locally networked devices. For instance, the one or more devices 150, 160 can include a cell phone, a smart phone, a tablet computing device, a laptop computing device, a personal digital assistant ("PDA"), a wearable computing device, or any other stationary or portable device configured to communicate with other devices over a network. For example, implementations can include electronic organizers, multimedia devices, portable music players, communication devices, and handheld, wearable, or portable electronic devices for gaming and/or data organization. The one or more mobile devices 150, 160 may be the same or can include mobile devices of different types. The one or more mobile devices 150, 160 may also perform functions unrelated to the monitoring system, such as placing personal telephone calls, playing music, playing video, displaying pictures, browsing the Internet, maintaining an electronic calendar, etc.

In some implementations, the one or more mobile devices 150, 160 can communicate with the monitor control unit 110 via the communication link. For instance, the one or more mobile devices 150, 160 can communicate with the monitor control unit 110 using various local wireless protocols, such as Wi-Fi, Bluetooth, Z-Wave, ZigBee, HomePlug (Ethernet over powerline), or wired protocols such as Ethernet, USB, and other wired protocols based on the RS232, RS485, and/or RS422 standards. The one or more mobile devices 150, 160 can connect locally to the monitor control unit 110 and/or other components of the monitoring system 200 (e.g., one or more cameras, sensors, or other components). The local connection can improve the speed of communications because communicating through the network 105 with a remote server (e.g., the central monitoring station 170), can be slower.

Although the one or more mobile devices 150, 160 are shown communicating with the monitor control unit 110, in some implementations, the one or more mobile devices 150, 160 can communicate directly with the cameras, sensors, and other components that are in communication with the monitor control unit 110. In some implementations, the one or more mobile devices 150, 160 replace the monitor control unit 110 and perform the functions of the monitor control unit 110 for local control and long range or offsite communication and/or control.

In other implementations, the one or more mobile devices 150, 160 may receive data from the monitor control unit 110 through the network 105. The one or more mobile devices 150, 160 may either receive data from the monitor control unit 110 through the network 105, or from the central monitoring station 170 and transmit or relay the data to the monitor control unit 110 through the network 105. In this regard, the central monitoring station 170 may facilitate communications between the one or more mobile devices 150, 160 and the monitor control unit 110.

Although the one or more mobile devices 150, 160 are shown in FIG. 2 as being connected to the network 105, in some implementations, the one or more mobile devices 150, 160 are not connected to the network 105. In such implementations, the one or more mobile devices 150, 160 may communicate directly with one or more of the monitoring system components without requiring a network connection (e.g., using a Bluetooth connection, or a near-field communication (NFC) connection).

In some implementations, the one or more mobile devices 150, 160 are used in conjunction with only local cameras, sensors, and other components of the system 100. In such implementations, the system 100 only includes the one or more mobile devices 150, 160 and the sensors 140. The one or more mobile devices 150, 160 may receive data directly from the sensors 140, and can send data directly to the sensors 140. The one or more mobile devices 150, 160 may provide the appropriate interfaces and/or processing to provide for control of the system 100, including capabilities to modify system preferences, control system components, and/or respond to events detected by the system 100, etc.

The one or more mobile devices 150, 160 each include native control applications 142, 152, respectively. The native control applications 142, 152 may refer to software/firmware programs running on the corresponding device that enables the described features. The one or more mobile devices 150, 160 may load or install the native control application 142, 152 based on data received over the network 105 or data received from local media. The native monitoring application 142, 152 may run on the operating systems of the mobile devices 150, 160.

The central monitoring station 170 may be an electronic device configured to provide monitoring services and enable monitoring system configuration by exchanging electronic communications with the monitor control unit 110, the optical device 120, the HVAC system 130, the sensors 140, and/or the one or more mobile devices 150, 160 over the network 105. For example, the central monitoring station 170 may be configured to receive video data collected by the optical device 120 that includes one or more blink patterns produced by an output device of the HVAC system 130. In addition, the central monitoring station 170 can receive information related to the sensors 140 (e.g., network signal strength, installation status, etc.) through the monitor control unit 110.

The central monitoring station 170 may store data (e.g., video or image data obtained by cameras of the system 100, sensor data from sensors 140 of the system 100, or performance data from appliances or HVAC system components associated with the system 100) and can perform analysis of the stored data. Based on the analysis, the central monitoring station 170 may communicate with and control components of the system 100, such as one or more cameras, sensors, or other components of the sensors 140 that are connected to the monitor control unit 110 over the network 105.

In some implementations, the central monitoring station 170 may process the received video data and the blink pattern information produced by an output device of the HVAC system 130 in order to identify a system status associated with one or more components of the HVAC system 130. The central monitoring station 170 can include a video processing module that is configured to identify a wavelength of light produced by the output device and a frequency at which light is turned on and off over a period of time. The identified information can be used to reconstruct a digital blink pattern that is either human-readable (e.g., segmented line pattern), or capable of being processed by the central monitoring station 170 in order to identify a corresponding system status associated with the blink pattern. For example, the detected blink pattern can be converted into a set of finite parameter values that indicate attributes of the detected blink pattern (e.g., time-on interval, time-off interval, pattern repeat interval, etc.). The attributes can then be used to generate unique identifiers for each type of blink pattern. In this example, the central monitoring station 170 then stores a unique identifier for each type of blink pattern and then subsequently uses the unique identifier as an index within a repository (illustrated in FIG. 3) to identify a corresponding status for a detected blink pattern.

In some implementations, the central monitoring station 170 may be connected to the Internet over the network 105 and can access information at a website or database that is accessible on the Internet. Additionally, or alternatively, the central monitoring station 170 may store information at a local database or other data storage component and can access the stored information. For example, the central monitoring station 170 may access system component information relating to cameras, sensors, or other components of the system 100 at a website or database that is accessible via the Internet. The central monitoring station 170 may also access the manufacturer's device information relating to the HVAC system 130 in order to process blink pattern data collected by the optical device 120. For example, blink patterns that are unique to specific manufacturers can be aggregated in order to subsequently identify manufacturer-specific system statuses associated with a detected blink pattern.

FIG. 3 illustrates an example of a blink pattern repository 300. The repository 300 generally stores individual blink patterns detected by the optical device 120 and corresponding system and system status information. In the example depicted, the repository 300 stores a LED color associated with the LED indicator 134, a detected blink pattern, a device manufacturer, an associated system status, and a specified system action to be performed by the system 100 in response to detecting the indicated blink pattern. In this regard, in response to a detection of a particular blink pattern by the optical device 120, the monitor control unit 110 or the central monitoring station 170 can utilize the repository 300 to automatically perform a specified system action that is associated with the particular blink pattern.

In general, the repository 300 can be generated based on historical data of previously detected blink patterns of common HVAC systems or components, diagnoses relating to the previously detected blink patterns, and system actions performed to address the diagnoses. For example, the repository 300 can be generated based on compiling information associated with service records of one or more properties (e.g., service tickets, maintenance inspection information, and/or components repair histories). The compiled information can then be aggregated based on certain categories such as device type or device manufacturer and stored in individual records such that each record corresponds to a distinct blink pattern previously detected by the system 100 across multiple properties.

The repository 300 may be stored locally (e.g., on the monitor control unit 110, the optical device 120) or remotely (e.g., on the central monitoring station 170). In some implementations, the repository 300 may be periodically updated to include updated information associated with recently detected blink pattern data in one or more properties. For instance, in such implementations, the central monitoring station 170 may aggregate system activity data that includes detected blink patterns, identified system statuses and/or system actions take in response to a diagnosis over a period of time, and then provide updates to the repository 300 so that the number of individual blink patterns that are included within the repository 300 grows over time. In this regard, the system 100 can utilize system activity of similar HVAC components across multiple properties in order to improve the likelihood that a particular blink pattern detected within a certain property is likely to be included within the repository 300.

In the examples depicted in FIG. 3, records 302, 304, 306, 308, 310, and 312 each correspond to different individual blink patterns that were previously detected by the optical device 120. The information specified by the records 302-312 includes an LED color (e.g., wavelength of light), a blink pattern characterized by, for example, time-on interval, time-off interval and/or repeating pattern interval, associated system information (e.g., device manufacturer, system status), and a specified system action that is predicted to resolve a system diagnosis indicated by the system status. As described above, the specified system action can be determined based on historical service record information indicating previous actions taken to resolve a system status associated with the corresponding blink pattern.

As shown, the blink pattern data detected by the optical device 120 (e.g., the blink pattern data 104a illustrated in FIG. 1) can be represented in a digital format that is recognizable by a human (e.g., as a line segment pattern), or as a unique identifier based on values of parameters associated with a blink pattern. As an example, line segments within a stored line pattern can represent a time interval when the LED indicator 134 produces light, whereas spacing between repeating line segments within the stored line pattern can represent a time interval when the LED indicator 134 does not produce light.

The particular system action that is performed can be based on the severity of a problem condition indicated by the system status. For example, as illustrated in record 306, if a detected blink pattern indicates that the HVAC system 130 is operating functionally without requiring any maintenance, then the central monitoring station 170 may update the transmission record for alerts without sending an alert to the user 102. In this example, the data transmission record for monitoring operations is updated to reflect a detected blink pattern. Alternatively, as illustrated in record 302, if a detected blink pattern indicates that routine maintenance might be required to keep the system optimally operating functionally, then the central monitoring station 170 may update the service record for the user account to automatically schedule a maintenance operation without actually alerting the user and/or the service provider. In this example, because the system status indicates a low performance impact diagnosis, the system action does not notify the user of the update to the service record. In another example, as illustrated in record 304, if a detected blink pattern indicates that a high performance impact is detected for a particular component, then the central monitoring station 170 may transmit an alert notification to the user based on the severity of the performance impact associated with the system status. In this example, because there is a high likelihood of total system failure that may impose significant costs to the user if not addressed immediately, a high urgency is associated with the system action specified for the system status.

As discussed above, the blink pattern repository 300 includes records of multiple predetermined or known blink patterns. Each record can include one or more reference attributes for a known blink pattern, e.g., attributes that are verified and/or associated with device maintenance information. For example, attributes of a known blink pattern can be used as a distinctive identifier that allows the control unit 110 and/or the central monitoring station to identify a detected blink pattern based on determining that attributes of the detected blink pattern matches the attributes of a known blink pattern. Each record within the repository 300 may also indicate a status represented by a blink pattern. For example, if a blink pattern represents a signal for a particular maintenance operation, then the status can identify the maintenance operation. In some instances, the repository 300 also specifies a system action that has been previously performed in relation to a status. In the maintenance example, the system action specified in the record can be an action previously performed by a monitoring system to address the monitoring operation, e.g., transmitting a notification of the maintenance operation to a property owner, or scheduling a service appointment to perform the maintenance operation at the property.

Figure 4:
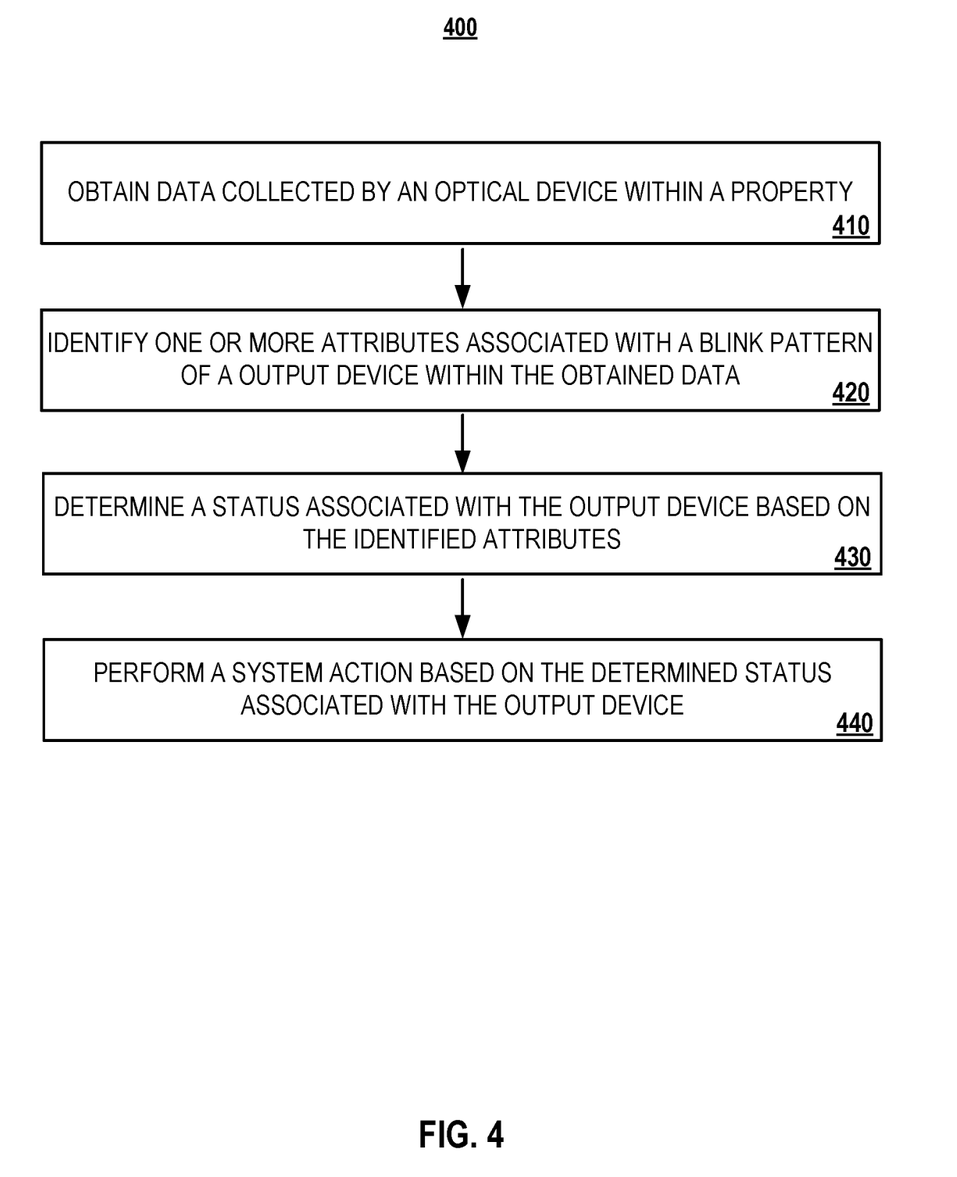
FIG. 4 illustrates an example of a process for automatically diagnosing issues associated with a monitoring system based on analyzing blink pattern data.

FIG. 4 illustrates an example of a process 400 for automatically diagnosing issues associated with a monitoring system based on analyzing blink pattern data. Briefly, the process 400 may include obtaining data collected by an optical device within a property (410), identifying one or more attributes associated with a blink pattern of a monitoring device within the obtained data (420), determining a status associated with the monitoring device based on the identified attributes (430), and performing a system action based on the determined status associated with the monitoring device (440).

In more detail, the process 400 may include obtaining data collected by an optical device within a property (410). For instance, the monitor control unit 110 or the central monitoring station 170 may obtain blink pattern data 104a collected by the optical device 120. As described above with respect to FIG. 1, the blink pattern data 104a can include, for example, a wavelength of light produced by the LED indicator 134 of an output device of a monitoring system such as the HVAC system 130. The blink pattern data 104a can also include other measured frequency and interval attributes such as a time interval for which the LED of the LED indicator 134 produces light, and a time interval for which the LED of the LED indicator 134 does not produce light.

The blink pattern data 104a is obtained based on processing the field of view within the raw video footage collected by the optical device 120 using optical recognition techniques. In some instances, the optical recognition techniques are performed by the monitor control unit 110 or the central monitoring station 170 after obtaining raw video footage from the optical device 120. In such implementations, the optical device 120 is simply configured to collect video footage based on detecting a possible blink pattern provided by the LED indicator 134. In other implementations, the optical device 120 is configured to use the optical recognition techniques to extract the blink pattern data 104a and then transmit the extracted data to monitor control unit 110, which then transmits the extracted data to the central monitoring station 170.

The process 400 may include identifying one or more attributes associated with a blink pattern of an output device within the obtained data (420). For instance, the optical device 120, the monitor control unit 110, or the central monitoring station 170 may identify attributes that characterize the blink pattern detected within the video footage collected by the optical device 120. For example, as described above, such attributes can include a color of the produced light (e.g., the measured wavelength of light), a time interval for which light is produced by the LED of the LED indicator 134, and/or a time interval for which is light is not produced by the LED of the LED indicator 134. In instances where the detected blink pattern is a sequence of a distinct reoccurring pattern, the attributes can further include a time interval corresponding to the length of the reoccurring pattern, as well as a sequence of light events that represents the reoccurring pattern.

The process 400 may include determining a status associated with the output device based on the identified attributes (430). For instance, the monitor control unit 110 or the central monitoring station 170 may determine a system status associated with an output device corresponding to the detected blink pattern. As described previously, the system status can be determined based on compared a determined blink pattern to the blink patterns stored in a repository (e.g., the repository 300) that maps individual blink patterns to system and system status information. In some instances, if a detected blink pattern matches a stored blink pattern within the repository, then the system status of the output device may be determined to be the system status specified within the record of the stored blink pattern. In other instances, in addition to comparing the detected blink pattern and the stored blink patterns, the monitor control unit 110 or the central monitoring station 170 may also compare system information of the output device (e.g., manufacturer, device type, etc.) to the system information specified within the record for the stored blink patterns that match the detected blink pattern. In such instances, the number of false positive matches maybe reduced due to similar blink patterns being produced by devices of different manufacturers that use the same blink pattern to indicate different system statuses.

In some implementations, the status identifies a likelihood that a failure condition for the device will occur. For example, the status for a HVAC system that has a partially functioning furnace can indicate a 70% that the entire HVAC system will need to be replaced due to system-wide malfunctioning based on the present condition of the furnace. The status can also identify a predicted time point for occurrence of the failure condition. For example, the status for the HVAC system can also indicate that the HVAC system will malfunction in September of the present year because the furnace of the HVAC system is likely to experience excessive stress due to seasonal changes in ambient temperature. In such implementations, the system action can be transmitting a reminder to the property owner to replace the furnace of the HVAC system to prevent system-wide malfunctioning. The control unit 110 and/or the central monitoring system 170 can transmit the reminder in July or August of the present year (i.e. before September of the present year when the HVAC system is predicted to malfunction) so that the user can replace the furnace instead of having to replace the entire HVAC system later on.

The process 400 may include performing a system action based on the determined status associated with the output device (440). For instance, in response to identifying a system status for a detected blink pattern within the repository 300, the monitor control unit 110 or the central monitoring station 170 may automatically perform a specified system action associated with the identified system status. For example, as illustrated in FIG. 1, in some instances, the system status can indicate a diagnosis for a problem relating to the operation of one or more system components. In response, the central monitoring station 170 may transmit a notification indicating the problem to either the user 102 of the property in which an HVAC system is located, a service provider for the HVAC system, or another entity that would benefit from being informed about potential problems relating to the operation of the HVAC system. In other examples, the central monitoring station 170 can perform other actions such as updating a service record for the user account to schedule a routine maintenance appointment.

In some implementations, the control unit 110 and/or the central monitoring station 170 can automatically generate the blink pattern repository (e.g., without user input that manually associates blink patterns to statuses and system actions). In such implementations, the control unit 110 and/or the central monitoring station 170 may obtain historical monitoring data from multiple properties. The multiple properties can include properties that are monitored by the central monitoring station 170, e.g., properties that receive monitoring services from an organization that manages the central monitoring station 170. Alternatively, the multiple properties can include properties that share a common attribute, e.g., properties of the same property type, properties that have the same or similar monitored devices, etc.

The historical data can include previously detected blink patterns for devices within each of the multiple properties. For example, the historical data can include all blink patterns detected for devices during a specified time period (e.g., one year) and attributes previously identified got the detected blink patterns. The historical data can maintenance data for the devices whose blink patterns were captured, e.g., records of service appointments, records of device repairs or replacements, etc.

The control unit 110 and/or the central monitoring station 170 processes the contents of the historical data for each property, e.g., blink pattern data and maintenance data, to identify associations between maintenance events such as device repair or replacement and detected blink patterns. For example, the control unit 110 and/or central monitoring station 17) may identify an association if maintenance data for a property indicates that a device repair operation was performed a week after a detected blink pattern produced by the device. In some instances, this association can initially be determined automatically and then verified manually by a system administrator such as an employee of the organization that manages the central monitoring station 170.

In some instances, the control unit 110 and/or the central monitoring station 170 identifies statuses and system actions for blink patterns within the historical data based on data collected by sensors within a property immediately before, during, or immediately after a time period during which a blink pattern is detected. For example, the control unit 110 and/or the central monitoring station 170 processes set point data collected by thermostat of a property in parallel with blink pattern data produced by an associated HVAC system of the property during a three-month time period. In this example, if the set point data indicates large fluctuations in measured air temperature regardless of a constant set point temperature, then this information can be used to determine that the blink pattern indicates that a temperature regulator of the HVAC system is malfunctioning.

The control unit 110 and/or the central monitoring station 170 uses the associations between maintenance data and blink pattern data to generate records within the blink pattern repository to identify statuses and/or system actions that correspond to the previously blink patterns. For example, if a previously detected blink pattern for a HVAC system is associated with a service appointment for checking air flow and vent replacement, then the control unit 110 and/or the central monitoring station 170 may identify a status specifying "improper air flow" and a system action where a notification specifying that vent replacement may be needed is provided to a property owner. The identified status and system action is stored within a record for the previously detected blink pattern within the blink pattern repository. In this example, the control unit 110 and/or the central monitoring station 170 determines that the status and the system action within the record corresponds to a subsequently detected blink pattern if the attributes of the subsequently detected blink pattern matches the attributes specified in the record.

In some implementations, the status determined for a HVAC system 130, as discussed above, can be determined based on sensor data collected by other sensors within the property 101, such as the sensors 140. In such implementations, the control unit 110 and/or the central monitoring station 170 may obtain data collected by the sensors 140 in addition to blink pattern data 104a collected by the optical device 120. The obtained sensor data can be used to determine other environmental conditions and/or factors that can represent and/or impact a status determined for the HVAC system 130. The status determined for the HVAC system 130 can be based on the obtained sensor data and the system action corresponding to the determined status can be determined based on identifying a system action that is predetermined to correspond to the obtained sensor data. For example, set point temperature data collected by a thermostat associated with the HVAC system 130 can be used to determine and/or infer a status representing that vents of the HVAC system 130 require cleaning. In this example, the monitor control unit 110 and/or the central monitoring station 170 can use the obtained set point temperature data to assign the determined system action to the blink pattern 104a collected by the optical device 120 within a record of the blink pattern repository. In this respect, when the same blink pattern is subsequently detected by the optical device 120, the system can use the assignment within the blink pattern repository to determine the system action to be performed.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially designed application-specific integrated circuits (ASICs).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

What is claimed is:

1. A method comprising:
obtaining video data indicating a blink pattern of a device within a property;
identifying one or more attributes of the blink pattern based on processing the obtained video data;
determining a status for the device based at least on the one or more identified attributes;
determining a system action corresponding to the determined status; and
performing the system action corresponding to the determined status.

2. The method of claim 1, wherein:
the one or more attributes of the blink pattern comprises at least one of a light emitting diode (LED) color, a blinking frequency, or a time delay between consecutive blinks.

3. The method of claim 1, wherein determining the system action comprises:
accessing a blink pattern repository that identifies multiple predetermined blink patterns, the blink pattern repository comprising, for each of the multiple predetermined blink patterns, (i) one or more reference attributes, and (ii) a corresponding system action;
determining that at least one of the identified attributes for the blink pattern matches a reference attribute for a particular blink pattern from among the multiple predetermined blink patterns; and
selecting a particular system action corresponding to the particular blink pattern based on determining that at least one of the identified attributes for the blink pattern matches the reference attribute for the particular blink pattern.

4. The method of claim 1, wherein:
the status identifies a maintenance operation for the device; and
the system action comprises transmitting, to a computing device of a user associated with the property, a communication identifying data associated with the maintenance operation for the device.

5. The method of claim 1, wherein:
the status identifies a maintenance operation for the device; and
the system action comprises transmitting, to a server system of a service provider of the device, a request to schedule a service appointment at the property.

6. The method of claim 1, wherein:
the status identifies (i) a likelihood of a failure condition for the device will occur, and (ii) a predicted time point for occurrence of the failure condition; and
the system action is performed prior to the predicted time point for occurrence of the failure condition.

7. The method of claim 1, further comprising:
obtaining historical data for multiple properties, the historical data indicating blink patterns for one or more devices within each of the multiple properties; and
generating a blink pattern repository including one or more records for each of the one or more devices, each record identifying (i) one or more attributes of a blink pattern, and (ii) a system action predetermined to correspond to the blink pattern.

8. The method of claim 7, wherein:
the historical data for a particular property from among the multiple properties includes (i) a blink pattern for a particular device within the particular property, and (ii) a maintenance data for the particular device; and
generating the blink pattern repository comprises:
identifying a maintenance operation performed for the particular device within the maintenance data;
determining that the maintenance operation corresponds to the blink pattern for the particular device; and
generating a record for the particular device within the blink pattern repository, the record associating the blink pattern for the particular device and the maintenance operation that is determined to correspond to the blink pattern for the particular device.

9. The method of claim 1, further comprising:
obtaining sensor data collected by one or more sensors located within the property;
determining the status for the device based on the obtained sensor data; and
wherein determining the system action corresponding to the determined status comprises:
identifying a system action predetermined to correspond to the obtained sensor data,
generating, within a blink pattern repository, a record that assigns the identified system action to the determined status for the device.

10. A system comprising:
one or more computers; and
one or more storage devices storing instructions that are operable, when executed by one or more computers, to cause the one or more computers to perform operations comprising:
obtaining video data indicating a blink pattern of a device within a property;
identifying one or more attributes of the blink pattern based on processing the obtained video data;
determining a status for the device based at least on the one or more identified attributes;
determining a system action corresponding to the determined status; and
performing the system action corresponding to the determined status.

11. The system of claim 10, wherein:
the one or more attributes of the blink pattern comprises at least one of a light emitting diode (LED) color, a blinking frequency, or a time delay between consecutive blinks.

12. The system of claim 10, wherein determining the system action comprises:
accessing a blink pattern repository that identifies multiple predetermined blink patterns, the blink pattern repository comprising, for each of the multiple predetermined blink patterns, (i) one or more reference attributes, and (ii) a corresponding system action;
determining that at least one of the identified attributes for the blink pattern matches a reference attribute for a particular blink pattern from among the multiple predetermined blink patterns; and
selecting a particular system action corresponding to the particular blink pattern based on determining that at least one of the identified attributes for the blink pattern matches the reference attribute for the particular blink pattern.

13. The system of claim 10, wherein:
the status identifies a maintenance operation for the device; and
the system action comprises transmitting, to a computing device of a user associated with the property, a communication identifying data associated with the maintenance operation for the device.

14. The system of claim 10, wherein:
the status identifies a maintenance operation for the device; and
the system action comprises transmitting, to a server system of a service provider of the device, a request to schedule a service appointment at the property.

15. The system of claim 10, wherein:
the status identifies (i) a likelihood of a failure condition for the device will occur, and (ii) a predicted time point for occurrence of the failure condition; and
the system action is performed prior to the predicted time point for occurrence of the failure condition.

16. A non-transitory computer-readable medium storing software comprising instructions executable by one or more which, upon such execution, cause the one or more computers to perform operations comprising:
obtaining video data indicating a blink pattern of a device within a property;
identifying one or more attributes of the blink pattern based on processing the obtained video data;
determining a status for the device based at least on the one or more identified attributes;
determining a system action corresponding to the determined status; and
performing the system action corresponding to the determined status.

17. The device of claim 16, wherein:
the one or more attributes of the blink pattern comprises at least one of a light emitting diode (LED) color, a blinking frequency, or a time delay between consecutive blinks.

18. The device of claim 16, wherein determining the system action comprises:
accessing a blink pattern repository that identifies multiple predetermined blink patterns, the blink pattern repository comprising, for each of the multiple predetermined blink patterns, (i) one or more reference attributes, and (ii) a corresponding system action;

determining that at least one of the identified attributes for the blink pattern matches a reference attribute for a particular blink pattern from among the multiple predetermined blink patterns; and selecting a particular system action corresponding to the particular blink pattern based on determining that at least one of the identified attributes for the blink pattern matches the reference attribute for the particular blink pattern.

19. The device of claim 16, wherein:

the status identifies a maintenance operation for the device; and the system action comprises transmitting, to a computing device of a user associated with the property, a communication identifying data associated with the maintenance operation for the device.

20. The device of claim 16, wherein:

the status identifies a maintenance operation for the device; and the system action comprises transmitting, to a server system of a service provider of the device, a request to schedule a service appointment at the property.

\* \* \* \* \*